United States Patent [19]

Newbower

[11] 4,380,237
[45] Apr. 19, 1983

[54] APPARATUS FOR MAKING CARDIAC OUTPUT CONDUCTIVITY MEASUREMENTS

[75] Inventor: Ronald S. Newbower, Acton, Mass.

[73] Assignee: Massachusetts General Hospital, Boston, Mass.

[21] Appl. No.: 293,198

[22] Filed: Aug. 17, 1981

Related U.S. Application Data

[63] Continuation of Ser. No. 99,710, Dec. 3, 1979, abandoned.

[51] Int. Cl.³ .............................................. A61B 5/02
[52] U.S. Cl. .................................... 128/693; 128/734
[58] Field of Search ................... 128/419 P, 632, 635, 128/668, 691–693, 713, 734, 736

[56] References Cited

U.S. PATENT DOCUMENTS

| | | | |
|---|---|---|---|
| 2,661,734 | 12/1953 | Holzer et al. | 128/734 |
| 3,149,627 | 9/1964 | Bagno | 128/693 |
| 3,566,233 | 2/1971 | Kahn et al. | 128/734 |
| 3,572,315 | 3/1971 | Cullen | 128/632 |
| 3,994,284 | 11/1976 | Voelker | 128/693 |
| 3,995,623 | 12/1976 | Blake et al. | 128/419 P |

Primary Examiner—William E. Kamm
Attorney, Agent, or Firm—Weingarten, Schurgin, Gagnebin & Hayes

[57] ABSTRACT

An improved catheter probe includes a conductivity sensor comprising four electrodes configured and spaced to be electrically coupled together by vascular fluids. A current source is provided for driving current through the vascular fluid between one pair of electrodes, and voltage sensing means is provided for measuring the voltage between the other pair of electrodes. In the preferred embodiment, the electrodes are closely spaced, substantially parallel electrodes oriented along the longitudinal direction of the catheter and transversely spaced apart by a distance which is small compared to the diameter of the catheter. The longitudinal length of the electrodes is chosen to be large as compared to the transverse spacing. The preferred current source is an isolated AC source, and the preferred voltage detection means is a phase sensitive voltage detector selectively responsive to the frequency and phase of the current source.

12 Claims, 7 Drawing Figures

APPARATUS FOR MAKING CARDIAC OUTPUT CONDUCTIVITY MEASUREMENTS

This is a continuation of application Ser. No. 099,710, filed Dec. 3, 1970, now abandoned.

FIELD OF THE INVENTION

This invention relates to improved apparatus for measuring the conductivity of vascular fluids. More particularly, it relates to an improved catheter probe having an electrode configuration and an electronic detection circuit for accurately measuring the conductivity of vascular fluids.

BACKGROUND OF THE INVENTION

Apparatus for measuring the electrical conductivity of vascular fluids is of potentially great value of diagnosing and monitoring critical conditions of the heart, lungs and blood. Such apparatus typically comprises a catheter cardiac probe including a pair of ring-like electrodes longitudinally spaced apart along the catheter. A small voltage is applied between the two electrodes, and the resulting current flow provides a measure of the conductivity of the vascular fluid between the two electrodes. In typical operation, a bolus of hyptertonic saline solution having a conductivity greater than that of blood is injected upstream of the electrodes. The passage of the bolus through the heart is monitored by measuring downstream the perturbation in conductivity of the vascular fluids. The rate at which the bolus passes and the manner of its passage provide useful measures of cardiac output.

In contrast to relatively slow conventional techniques based on measurements of thermal dilution, measurements of conductivity dilution are sufficiently fast that the conductivity variation can be measured for each separate beat of the heart. In addition, measurements of conductivity dilution can be used to supplement measurements of thermal dilution to obtain valuable information concerning the thermal mass of the tissues surrounding the vascular system. A potentially valuable application of such apparatus involves a comparison of the conductivity perturbation with the thermal perturbation to provide a measure of potentially dangerous water build-up in the lungs.

Unfortunately, prior art techniques for measuring the conductivity of vascular fluids have been inaccurate and inconsistent. As a consequence, despite the fact that conductivity sensing techniques were first used to measure cardiac output nearly 80 years ago, this potentially valuable technique has long been neglected as inherently unreliable.

SUMMARY OF THE INVENTION

The present inventor has recognized that one or more of three major sources of error have been present in prior approaches to measuring cardiac output conductivity: [1] wall effects comprising restrictions in the current flow path between electrodes when the probe is near a vascular wall; [2] interface impedance comprising the impedances at the interface between the electrodes and the vascular fluids; and [3] conductivity perturbations due to local fluctuations of red cell concentration near the electrodes.

In accordance with the invention, an improved catheter probe for overcoming these sources of error includes a conductivity sensor comprising four electrodes configured and spaced to be electrically coupled together by vascular fluids. A current source is provided for driving current through vascular fluids between one pair of electrodes, and voltage sensing means is provided for measuring the voltage between the other pair of electrodes. In the preferred embodiment, the electrodes are closely spaced, substantially parallel electrodes oriented along the longitudinal direction of the catheter and transversely spaced apart by a distance which is small compared to the diameter of the catheter. The longitudinal length of the electrodes is chosen to be large as compared to the transverse spacing. The preferred current source is an isolated AC source, and the preferred voltage detection means is a phase sensitive voltage detector selectively responsive to the frequency and phase of the current source.

BRIEF DESCRIPTION OF DRAWINGS

The nature, advantages and various additional features of the invention will appear more fully upon consideration of the illustrative embodiments now to be described in detail in connection with the accompanying drawings.

In the drawings.

For convenience of reference the same structural elements are designated by the same reference numerals throughout the drawings.

DETAILED DESCRIPTION OF THE DRAWINGS

Figure 1:
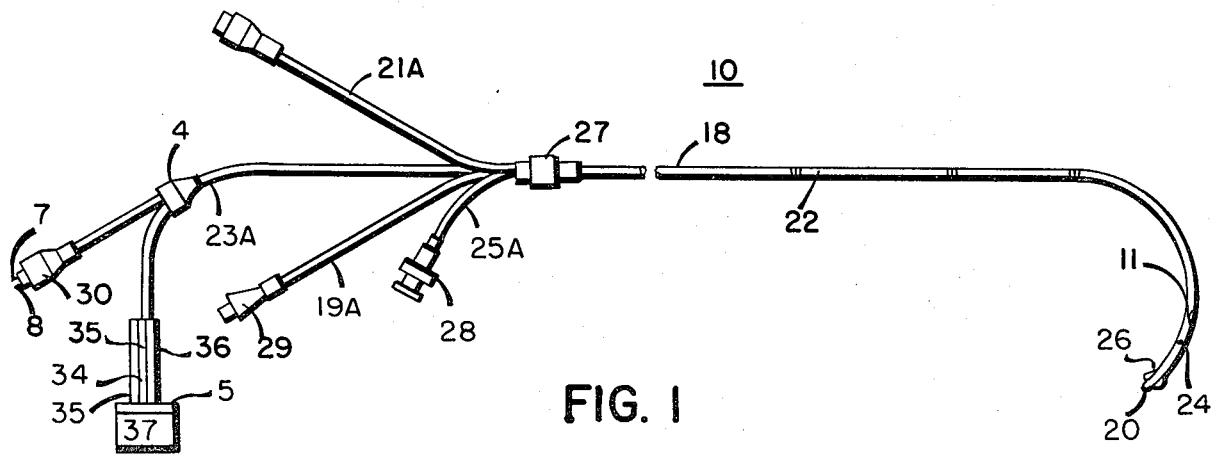
FIG. 1 is a perspective view of a preferred embodiment of an improved catheter probe in accordance with the invention.

Referring to the drawings, FIGS. 1 and 2 illustrate an improved catheter cardiac probe in accordance with the preferred embodiment of the invention. In substance, the improved catheter probe 10 comprises a conventional flexible catheter probe modified by the inclusion of a four-electrode conductivity sensor 11 and lead wires 33 through 36 to connect the electrodes to appropriate measuring circuitry 37, as described in greater detail hereinafter.

Figure 2A:
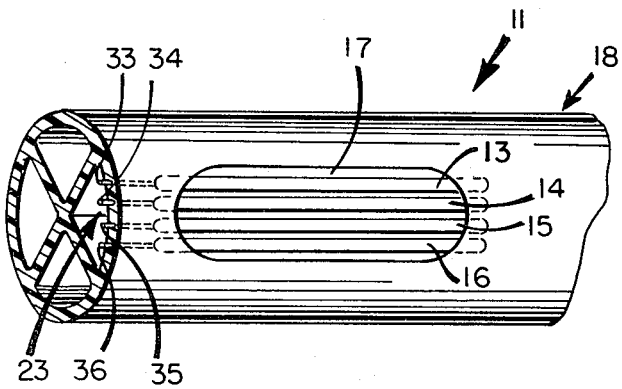
FIGS. 2A and 2B are enlarged plane and cross-sectional views of the preferred conductivity sensing portion of the probe of FIG. 1.

The conductivity sensor 11, as best shown in FIG. 2A, comprises four electrodes 13, 14, 15 and 16 which are spaced sufficiently close together that they are electrically coupled together when immersed in vascular fluids. The electrodes are preferably elongated parallel electrodes oriented with their major dimensions along the longitudinal direction of the catheter 10. The electrodes are preferably transversely spaced apart by center-to-center distances which are small compared to the diameter of the catheter and preferably less than about 0.1 millimeter. Their length in the longitudinal direction is preferably substantially greater than their transverse spacing and advantageously in excess of about 0.25 cm. The electrodes can be conveniently formed of goldplated copper on a flexible insulating substrate such as Kapton using conventional thick film circuit techniques.

Figure 2B:
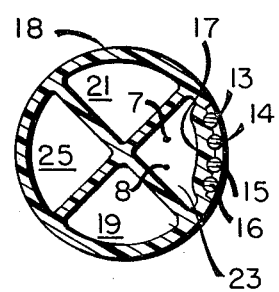

The catheter portion of the probe can conveniently comprise a conventional four lumen (longitudinally extending chamber) thermodilution catheter of the Swan-Ganz type such as Swan-Ganz Flow-Directed Thermodilution Catheter, Model 93A-131-7F marketed by Edward Laboratories, Inc., Santa Ana, Calif. 92711. As best shown in FIG. 1 and FIG. 2B, such as catheter comprises a four lumen tube 18 comprising a distal lumen 19 terminating at the tip 20 of the catheter, a proximal lumen 21, including a proximal injection port 22 approximately 30 cm from the tip 20, a thermistor lead lumen 23 for enclosing electrical leads to a thermistor 24 positioned approximately 4 cm from tip 20, and a balloon inflation lumen 25 terminating in a balloon 26 adjacent the tip. The four lumens 19, 21, 23 and 25 of tube 18 are conveniently coupled to four separate tubes 19A, 21A, 23A, and 25A, respectively, via a coupling connector 27, and appropriate terminations are provided for the separate tubes, including a balloon inflation valve 28, a distal lumen hub 29 and a thermistor lead connector 30. The conventional structure and operation of such a catheter is described in Swan, et al., "Use of Balloon Flotation Catheter in Critically Ill Patients", 55 Surg. Clin. North Am. 501-520 (1975) which is incorporated herein by reference.

In the preferred form of the present invention, the conventional catheter is modified by forming an additional port 11 in thermistor lead lumen near thermistor 24, preferably within about 1.0 cm of the thermistor. In addition to the thermistor leads 7 and 8, four additional insulated leads 33, 34, 35 and 36 are threaded through the thermistor lead lumen 23 and are electrically connected to respective ones of electrodes 13, 14, 15 and 16. The substrate 17 is fastened across the port with epoxy, sealing the port off with the electrodes facing outwards. The exposed adhesive is then covered with a varnish of minimal thrombogenicity, such as polyurethane, to obtain a smooth surface producing minimal clotting. The electrodes are thus mounted in position for exposure to vascular fluids and connected by leads via coupling connector 4 and four-terminal connector 5 to the conductivity measuring circuit 37.

Figure 3:
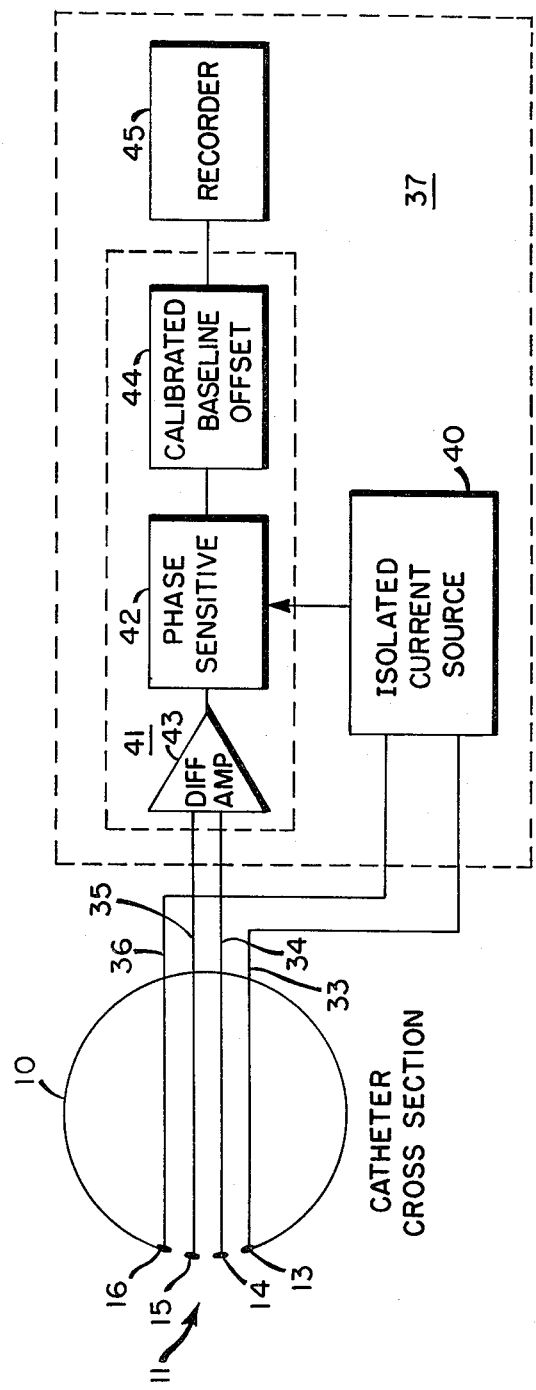
FIG. 3 is a schematic diagram of a preferred detection circuit used in connection with the probe of FIG. 1.

FIG. 3 schematically illustrates a preferred conductivity-measuring circuit for use with the improved probe of FIG. 1. In substance, the conductivity-measuring circuit comprises a current source 40 for driving a known and physiologically safe current between outer electrodes 13 and 16 and high impedance detection means 41 for measuring the voltage drop between inner electrodes 14 and 15 without drawing current sufficiently large to cause an error due to the source impedance of the voltage sensing electrodes. Typically the current drawn by the detection means should be less than a few nanoamps.

In the preferred embodiment, the current source is an isolated source of AC current having a frequency in the range between 1 KHz and 10 KHz and an rms current in the range between 5 microamps and 50 microamps. In this specific embodiment the frequency is about 2.5 KHz and the current is about 10 microamps.

The preferred voltage detector 41 comprises, in essence, a phase-sensitive detector 42 responsive to a reference signal from the current source for measuring voltage modulation of a voltage signal between inner electrodes 14 and 15 corresponding in phase and frequency to the current source. A differential amplifier 43 coupled between the electrodes and the detector 42 effectively isolates the electrodes so that no appreciable current flows through them, and a calibrated baseline offset 44 can optionally be provided to offset the conductivity of unaltered blood in conductive indicator tests. In experimental apparatus, applicant has used a Princeton Applied Research Lock-In Amplifier, Model 128A to perform the functions of detector 42, high impedance amplifier 43 and offset 44. A recorder 45 can be connected to the output to record the conductivity measurement as a function of time.

Figure 4:
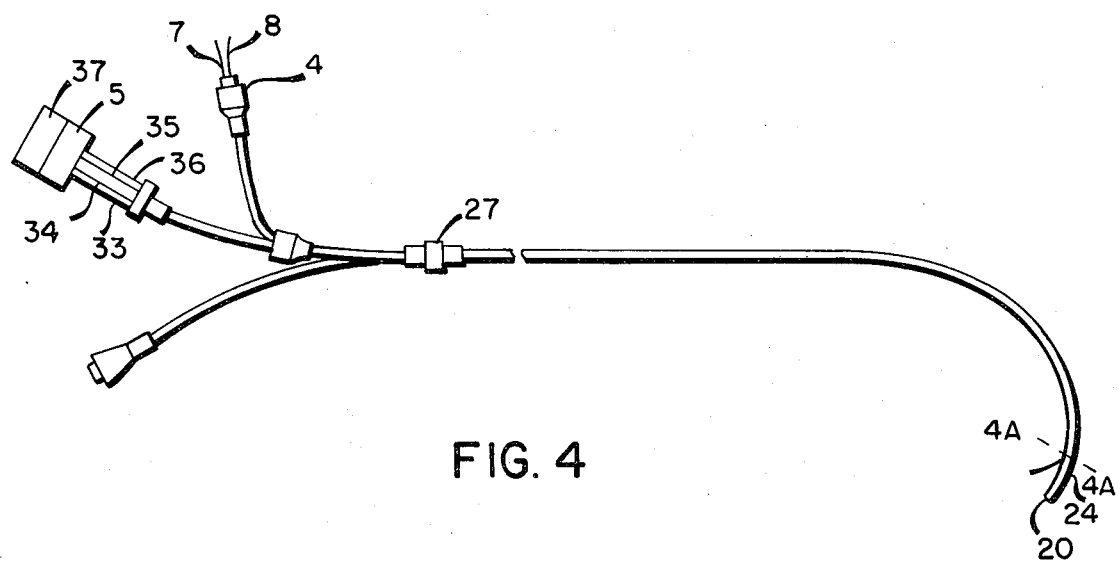
FIG. 4 is a perspective view of an alternative embodiment of a catheter probe in accordance with the invention.

FIG. 4 is a perspective view of an alternative embodiment of a catheter probe in accordance with the invention in the form of a central arterial catheter. This catheter is similar to the one shown in FIG. 1 except that it omits the balloon and the injection port. It typically includes a pressure port 20, a conductivity sensor 11 and a thermistor 24 as described above, near the tip. The thermistor can optionally be omitted for some applications.

Figure 5:
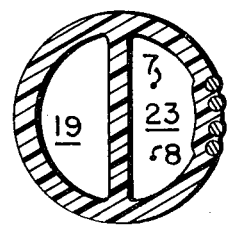
FIG. 5 is an enlarged cross-sectional view along the line 4A—4A' of the probe of FIG. 4.

As shown in FIG. 5, the arterial catheter of FIG. 4 comprises a two-lumen tube with leads 33, 34, 35 and 36 taken through the thermistor lead lumen 23 and fluid for pressure measurement taken through the other lumen 19.

The arterial catheter tube can be either flexible or rigid in accordance with principles well known in the art.

Figure 6:
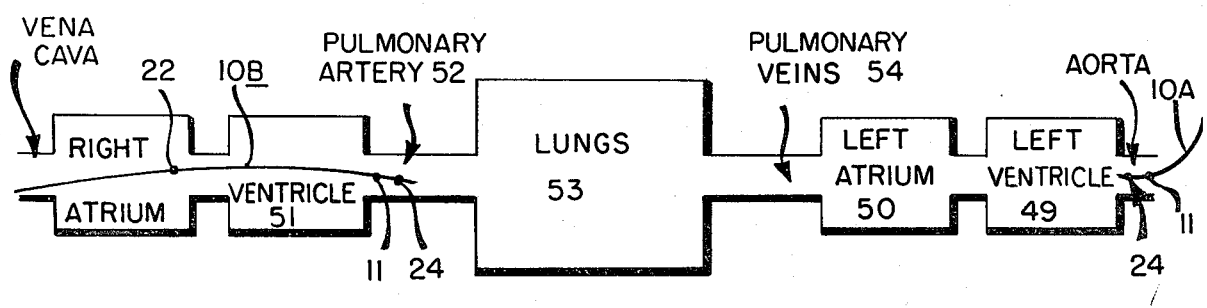
FIG. 6 is a schematic diagram showing a typical use of the probes of FIG. 1 and FIG. 4.

FIG. 6 is a schematic diagram illustrating a typical use of improved catheter probes 10A and 10B in accordance with the invention to monitor passage of a conductive ionic indicator through the lungs. In accordance with positioning techniques well known in the art, an arterial catheter 10A as shown in FIG. 5 is positioned in the vascular system in such a manner that the condutivity sensor 11 is in the aorta near the left ventricle 49 of the heart. A second catheter 10B of the type shown in FIG. 1 is positioned with its thermal and conductivity sensors 24 and 11 in the pulmonary artery near the right ventricle 51. A bolus of hyptertonic conductivity indicator, such as hypertonic saline solution or plasma, is then injected through port 22 into the vascular system. The conductivity sensor 11 of catheter 10B provides a useful measure of the output through the right side of the heart.

The indicator is then successively pumped through the pulmonary artery 52, the lungs 53, pulmonary veins 54, the left atrium 50 and the left ventricle 49 where it is detected by its alteration of the conductivity of the blood surrounding the conductivity sensor 11 of catheter 10A. The rate and manner of passage of the indicator provides an alternative measure of cardiac output.

To provide a measure of lung water, the hypertonic indicator can be provided at a known temperature substantially different from the blood temperature, and the temperature variation after passage through the lungs is detected by thermistor 24 on catheter 10A. A comparison of the temperature variation with the conductivity variation from both upstream and downstream catheters 10A and 10B provide a measure of lung water.

The advantages of the invention are manifold. Because the transverse spacing between adjacent electrodes is very small as compared to the diameter of the catheter (and therefore the portion of the vascular system containing the catheter), wall effects are minimized. And, because the electrodes are much longer than typical mean fluctuations in red cell density, local conductivity perturbations by red cells are minimized. Furthermore, since conductivity is measured by two electrodes which draw no appreciable current and the current is driven by current source, the effect of interface resistance on the conductivity measurement is minimized.

While the invention has been described in connection with a small number of specific embodiments, it should be understood that these are merely illustrative of the many other specific embodiments which can also utilize the principles of the invention. For example, while the preferred electrodes shown in the specification are substantially parallel linear structures, alternative electrode configurations such as concentric circles could alternatively be used. Similarly, while it is preferred that both voltage sensing electrodes be disposed between the two current supply electrodes, one or both sensing electrodes could alternatively be outside the current supply electrodes. Thus, numerous and varied devices can be made by those skilled in the art without departing from the spirit and scope of the present invention.

What is claimed is:

1. Apparatus for measuring the conductivity of vascular fluids within a vessel comprising:

a catheter having a predetermined diameter to fit within said vessel;

conductivity sensing means comprising at least two pairs of electrodes disposed on said catheter for contacting vascular fluids;

said electrodes comprising elongated conductive elements spaced apart by a predetermined distance which is both smaller than the diameter of the catheter and sufficiently small to reduce measurement fluctuations due to the fluid boundaries at the vascular walls, said conductive elements further having a length which is both larger than said predetermined distance and sufficiently large to reduce measurement fluctuations due to red blood cell density fluctuations;

means for supplying a known AC current between the electrodes of a first pair of electrodes; and means for measuring the voltage between the electrodes of the second pair in order to provide a measure of the conductivity of nearby vascular fluids.

2. Apparatus according to claim 1 wherein said electrodes are elongated conductive elements with their respective major dimensions longitudinally oriented with respect to said catheter.

3. Apparatus according to claim 1 wherein the spacing between said electrodes is constant over their length.

4. Apparatus according to claim 1 wherein said means for applying a known current comprises means for applying an AC current at a frequency in the range between 1 KHz and 10 KHz and at an rms value between 5 microamps and 50 microamps.

5. Apparatus according to claim 1 wherein said means for measuring the voltage comprises phase-sensitive detector means.

6. Apparatus according to claim 1 wherein said catheter further comprises means for measuring the temperature of vascular fluids.

7. Apparatus according to claim 1 wherein said catheter comprises a tube having a plurality of longitudinally extending internal chambers.

8. Apparatus according to claim 1 wherein said catheter is a cardiac catheter of the type comprising an elongated tube including a plurality of internal longitudinally extending chambers therein and a balloon adjacent one end.

9. Apparatus according to claim 1 wherein said catheter comprises a flexible tube.

10. Apparatus according to claim 1 wherein said catheter comprises a rigid tube.

11. Apparatus according to claim 1 wherein said electrodes are spaced apart by a distance less than about 0.1 millimeter and their length is in excess of about 0.25 cm.

12. Apparatus according to claim 1 further including a substrate mounted on said catheter wherein said electrodes are fabricated on said substrate.

* * * * *

UNITED STATES PATENT AND TRADEMARK OFFICE
CERTIFICATE OF CORRECTION

PATENT NO. : 4,380,237
DATED : April 19, 1983
INVENTOR(S) : Ronald S. Newbower

It is certified that error appears in the above—identified patent and that said Letters Patent is hereby corrected as shown below:

Column 1, line 6     "Dec. 3, 1970" should read --Dec. 3, 1979--;

Column 1, line 26     "hyptertonic" should read --hypertonic--;

Column 4, line 37     "condutivity" should read --conductivity--;

Column 4, line 41     "hyptertonic" should read --hypertonic--.

Signed and Sealed this

Eleventh Day of October 1983

[SEAL]

Attest:

GERALD J. MOSSINGHOFF

Attesting Officer     Commissioner of Patents and Trademarks